(12) United States Patent
Carson et al.

(10) Patent No.: US 6,191,142 B1
(45) Date of Patent: Feb. 20, 2001

(54) AROYL AMINOACYL PYRROLES FOR USE IN THE TREATMENT OF NEUROPATHIC PAIN

(75) Inventors: John R. Carson, Norristown; Philip M. Pitis, North Wales; Kathryn E. Rogers, Audubon, all of PA (US)

(73) Assignee: Ortho-McNeil Pharmaceutical, Inc., Raritan, NJ (US)

( * ) Notice: Under 35 U.S.C. 154(b), the term of this patent shall be extended for 0 days.

(21) Appl. No.: 09/505,916

(22) Filed: Feb. 17, 2000

Related U.S. Application Data

(60) Provisional application No. 60/120,477, filed on Feb. 18, 1999.

(51) Int. Cl.[7] .......................... A61K 31/47; A61K 31/40
(52) U.S. Cl. ................... 514/307; 514/235.5; 514/210.2; 514/217.08; 514/326; 514/397; 514/423; 514/427
(58) Field of Search .................................. 514/307, 326, 514/397, 423, 235.5, 210.2, 217.08, 427

(56) References Cited

U.S. PATENT DOCUMENTS

| 5,332,736 | 7/1994 | Carmosin et al. | 514/235.5 |
| 5,418,236 | 5/1995 | Carmosin et al. | 514/252 |

FOREIGN PATENT DOCUMENTS

98/07447   2/1998   (WO) .

*Primary Examiner*—Zinna Northington Davis

(57) ABSTRACT

Aroyl aminoacyl pyrroles are pharmaceutically useful in treating neuropathic pain, which includes utility for the treatment of neuropathic pain.

9 Claims, No Drawings

AROYL AMINOACYL PYRROLES FOR USE IN THE TREATMENT OF NEUROPATHIC PAIN

This application claims the benefit of Provisional Application Ser. No. 60/120,477, filed Feb. 18, 1999.

FIELD OF THE INVENTION

This invention relates to compounds useful in the treatment of neuropathic pain. More particularly, this invention relates to aroyl aminoacyl pyrroles that are useful in the treatment of neuropathic pain.

BACKGROUND OF THE INVENTION

The conditions grouped under the term neuropathic pain constitute an area of continuing medical need.

Neuropathic pain is defined as pain caused by aberrant somatosensory processing in the peripheral or central nervous system. Chronic or debilitating conditions, such as post-herpetic neuralgia and phantom limb syndrome, are categorized as neuropathic pain. Such conditions are widespread and cause unnecessary pain and suffering. Moreover, current methods of treating neuropathic pain are often inadequate and result in huge medical costs.

Anticonvulsants have been widely suggested for the treatment of neuropathic pain, Nadin Attal, et al., Effects of Gabapentin on the Different Components of Peripheral and Central Neuropathic Pain Syndromes: A Pilot Study, *Fr. Eur. Neurol.* 1998, 40(4), 191–200. Such compounds are believed to act preferentially on lancinating, shooting pain. Gabapentin induced a moderate and statistically significant relief of ongoing spontaneous pain, was particularly effective in reducing paroxysmal pain and was significantly effective on brush-induced and cold allodynia (a painful response to normally innocuous stimuli). In contrast, no effect on detection and pain thresholds to static mechanical and hot stimuli was observed. The study suggests that gabapentin is preferentially antihyperalgesic (mediates exaggerated responses to normally painful stimuli) and/or antiallodynic and similarly effective in pain due to peripheral nerve injuries or central lesions.

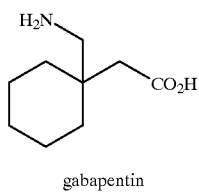

gabapentin

Other anticonvulsants have been useful in treating neuropathic pain, Richard P. Shank, et al., Anticonvulsant Derivatives Useful in Treating Neuropathic Pain, U.S. Pat. No. 5,760,007. As disclosed in this reference, studies conducted to evaluate the efficacy of the anticonvulsant topiramate in an animal model of neuropathic pain gave evidence of pharmacological activity in treating neuropathic pain.

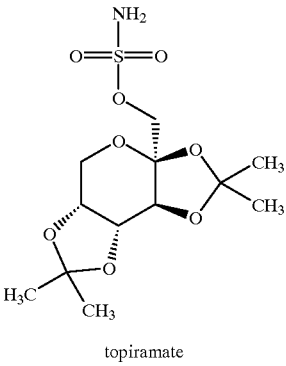

topiramate

Also, therapeutic compositions of anticonvulsants and non-toxic NMDA (N-methyl-D-aspartate) antagonists in neuropathic pain-alleviating amounts have been shown to block a major intracellular consequence of NMDA receptor activation, Frank S. Caruso, et al., Pharmaceutical Compositions Containing Anticonvulsants and NMDA Receptor Antagonists for Treating Neuropathic Pain, WIPO Patent No. 98/07447. This reference teaches the use of these anticonvulsants as suitable for use in this combination: lamotrigine, gabapentin, valproic acid, topiramate, famotidine, phenobarbital, diphenylhydantoin, phenytoin, mephenytoin, ethotoin, mephobarbital, primidone, carbamazepine, ethosuximide, methsuximide, phensuximide, trimethadione, benzodiazepine, phenacemide, acetazolamide, progabide, clonazepam, divalproex sodium, magnesium sulfate injection, metharbital, paramethadione, phenytoin sodium, valproate sodium, clobazam, sulthiame, dilantin, diphenylan and L-5-hydroxytryptophan.

The aroyl amino acyl pyrrole compounds of the present invention have been previously disclosed and taught as useful anticonvulsants, Richard J. Carmosin, John R. Carson, Philip M. Pitis, Anticonvulsant Aroyl Amino Acyl Pyrroles, U.S. Pat. No. 5,332,736. The compounds of the present invention, however, have not previously been shown as effective for the treatment of neuropathic pain. It is an object of the present invention to teach a method for the treatment of neuropathic pain using the compounds of the present invention.

SUMMARY OF THE INVENTION

Briefly, there is provided by the present invention a method for the treatment of neuropathic pain comprising the step of administering to a mammal suffering from such condition an effective amount, in a pharmaceutically acceptable carrier, of an active compound of the formula:

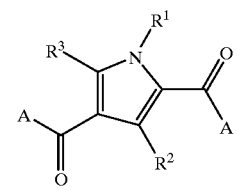

wherein,

A is simultaneously both

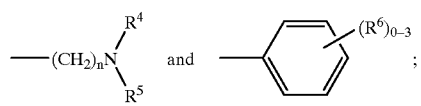

n is an integer from 1 to 5;
R$^1$ is selected from the group consisting of H and C$_{1-4}$alkyl;
R$^2$ and R$^3$ are selected from the group consisting of H and C$_{1-4}$alkyl;
R$^4$ and R$^5$ are independently selected from the group consisting of H, C$_{1-4}$alkyl, phenyl C$_{1-4}$ alkyl and substituted phenyl C$_{1-4}$ alkyl where the substituent is on phenyl and selected from the group consisting of methyl and methoxy, or in the alternative, are fused and together with said nitrogen form a heterocyclic ring selected from the group consisting of 4-[bis(4-fluorophenyl)methylene]-piperidin-1-yl, 1,2,3,4-tetrahydro-6,7-dimethoxy-isoquinolin-2-yl,

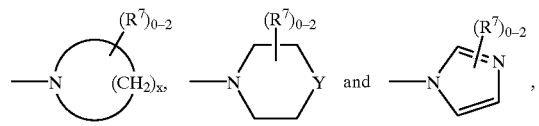

wherein Y is S or O, x is 3 to 7 and R$^7$ is selected from the group consisting of methyl and hydroxymethyl; and
R$^6$ is selected from the group consisting of halo, C$_{1-4}$ alkyl, C$_{1-4}$ alkoxy, hydroxy, nitro, amino, C$_{1-4}$ acylamino, cyano, trihalo C$_{1-4}$alkyl, C$_{1-4}$alkylsulfonyl, C$_{1-4}$alkylsulfinyl, and C$_{1-4}$ acyl,
including pharmaceutically acceptable acid addition salts thereof.

DETAILED DESCRIPTION OF THE INVENTION

The compounds of the present invention used in the treatment of neuropathic pain may be placed into two categories, those having benzoyl at the 2-position and those having benzoyl at the 4-position. Both categories of compounds may be prepared by variations of what is fundamentally the same reaction scheme.

Scheme 1 exemplifies the preparation of compounds having benzoyl at the 2-position. Referring to Scheme 1, in the first step a simple pyrrole A1 is acylated with an appropriately substituted benzoyl chloride B1 to produce benzoyl pyrrole C1. This acylation may be carried out by simply heating the benzoyl chloride and the pyrrole in an aprotic solvent followed by removing excess benzoyl chloride by reaction with a dibasic amine and extraction with HCl. Typical of the aprotic solvents which may be utilized are aromatic hydrocarbons, such as, benzene, toluene, xylene, chlorobenzene, nitrobenzene, etc.; paraffins, such as, methyl cyclohexane, octane, etc.; halocarbons, such as, methyl chloride, chloroform, tetrachloroethane, etc.; ethers, such as, diethyl ether, diglyme, etc.; ketones, such as, methyl ethyl ketone, cyclohexanone, etc.; esters, such as, ethyl butyrate, etc.; nitroalkanes, such as, nitropropane, etc.; or carbon disulfide. The temperature of the acylation will vary depending upon the desired rate of reaction and the substituents of pyrrole A1. Preferably the acylation is carried out at a temperature of from about 50 to 250° C. A suitable dibasic amine is dimethyl-3-aminopropyl amine. In the case where R$^1$ is hydrogen the acylation, as described, may not produce desirable yields. In this case, a Vilsmeier type acylation as employed by J. White and G. McGillivrey, J. Org. Chem., Vol. 42, pp 42–48, 1977 might be expeditiously employed. Subsequently, benzoyl pyrrole C1 is acylated at the 4-position in a Friedel-Crafts reaction with acid chloride D1 to produce 2-benzoyl4-alkanoyl pyrrole E1. The Friedel-Crafts reaction is carried out by refluxing the carboxylic acid chloride D1, in which X is Cl, Br or I, with product C1 in a solvent with a Friedel-Crafts reagent followed by treatment with HCl and evaporation of the solvent. Suitable Friedel-Crafts reagents include aluminum chloride, zinc chloride, BF$_3$ or TiCl$_4$. Suitable solvents include methylene chloride, 1,2-dichloroethane, carbon tetrachloride or chloroform. The temperature of reflux might vary between about 30 and 150° C. In the case where R$^6$ is amine, it will not survive the Friedel-Crafts reaction in good yield. Thus, it should be protected with well known protecting groups or present as a suitable precursor substituent, such as, nitro which can thereafter be converted to amine. In the third reaction, 2-benzoyl-4-alkanoyl pyrrole E1 is aminated with amine F1 to produce the desired 2-benzoyl-4-aminoalkanoyl pyrrole G1. The amination may be carried out by heating the reactants E1 and F1 neat or in a solvent to a temperature of from about 40 to 120° C. and preferably from about 50 to 90° C. Suitable solvents, where employed, include ethanol, i-propanol or toluene.

SCHEME 1

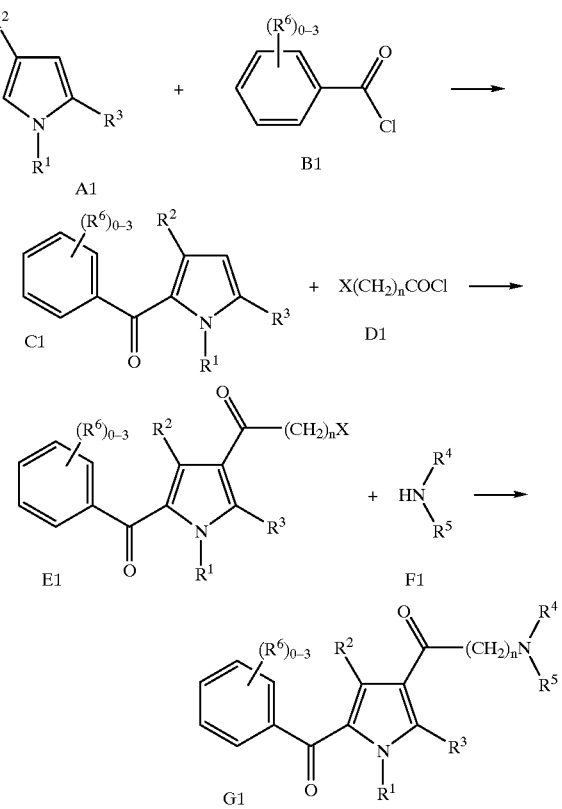

Scheme 2 exemplifies the preparation of compounds having benzoyl at the 4-position. Except for the specifics of the reactants, each step of Scheme 2 is analogous to the corresponding step of Scheme 1 with the reactions and description thereof being identical. Referring to Scheme 2, in the first step a simple pyrrole A2 is acylated with an appropriately substituted alkanoyl chloride B2 to produce alkanoyl pyrrole C2. Subsequently, alkanoyl pyrrole C2 is acylated at the 4-position in a Friedel-Crafts reaction with benzoic acid chloride D2 to produce 2-alkanoyl-4-benzoyl pyrrole E2. In the third reaction, 2-alkanoyl-4-benzoyl pyrrole E2 is aminated with amine F2 to produce the desired 2-aminoalkanoyl-4-benzoyl pyrrole G2.

SCHEME 2

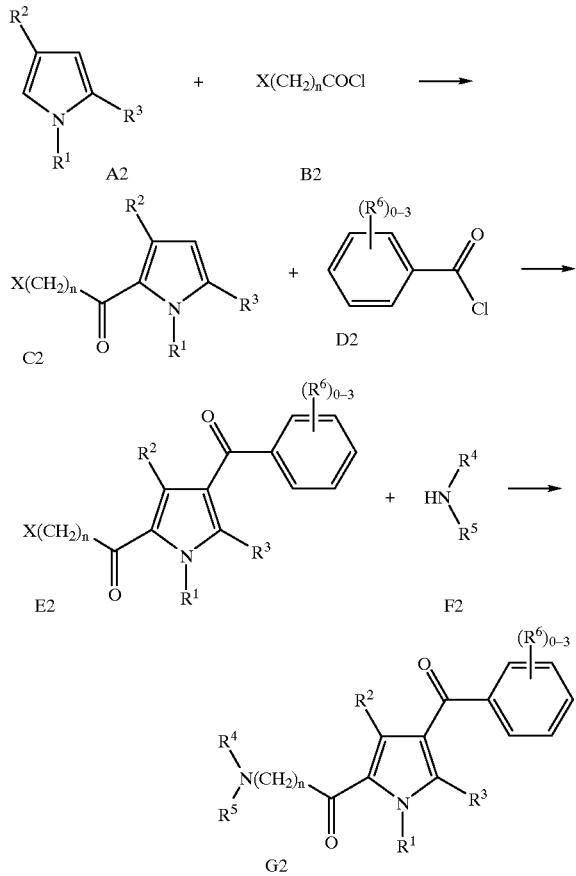

Preferred $R^1$ include hydrogen, methyl, ethyl, n-propyl and i-propyl. In the most preferred compounds, $R^1$ is methyl.

Preferred $R^2$ and $R^3$ include hydrogen, methyl, ethyl, n-propyl and i-propyl. In the most preferred compounds, $R^2$ and $R^3$ are hydrogen and methyl.

Preferred $R^4$ and $R^5$, where independently selected, include hydrogen, methyl, ethyl, n-propyl, i-propyl, benzyl and 2-phenyleth-1-yl where the phenyl ring may be mono- or di-substituted with a substituent selected from the group of methyl and methoxy. In the most preferred compounds, $R^4$ and $R^5$, where independently selected, are hydrogen, methyl and in at most one instance benzyl.

Preferred $R^4$ and $R^5$, where fused and depicted together with nitrogen, include 4-[bis(4-fluorophenyl)methylene]-piperidin-1-yl, 1,2,3,4-tetrahydro-6,7-dimethoxy-isoquinolin-2-yl,

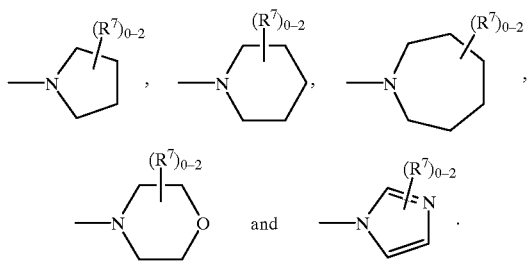

In the most preferred compounds, $R^4$ and $R^5$, where fused and depicted together with nitrogen, are piperidine-1-yl, pyrrolidin-1-yl, morpholin-1-yl and imidazol-1-yl.

Preferred $R^6$ include bromine, chlorine, methyl, ethyl, methoxy, ethoxy, hydroxy, nitro, amino, formylamino, acetylamino, cyano, perfluoromethyl, 3,3,3-trifluoropropyl, methylsulfonyl, methylsulfinyl, formyl, and acetyl. In the most preferred compounds, $R^6$ is non-existent, methyl or chloro.

The compounds herein readily form pharmaceutically acceptable acid addition salts. Such salts include hydrochlorides, sulfates, phosphates, methane sulfonates, fumarates, maleates, citrates, lactates, and the like. Those skilled in the art will readily recognize suitable methods for manufacture and use of the acid addition salts.

The compounds of the present invention are useful in the treatment of neuropathic pain. The use of the compounds in treating neuropathic pain was determined using an animal model. This model was developed and first described by S. H. Chung and J. M. Chung, An Experimental Model for Peripheral Neuropathy Produced by Segmental Spinal Nerve Ligation in the Rat, *Pain*, 1992, 50, 355–363 (referred to hereinafter as the "Chung Model").

Male Sprague-Dawley rats, weighing approximately 200 g each were anesthetized with isoflurane. The spinal nerve at the level of $L_5$ was exposed through an incision just left of the dorsal midline and tightly ligated with 6-0 silk. At various times after surgery, animals were tested for mechanical allodynia with von Frey hairs (monofilaments which are calibrated to bend under a certain amount of pressure, ranging from 0.41 to 15.1 g). In order to calculate a paw withdrawal threshold (PWT), tactile allodynia was measured by recording the pressure at which the affected paw was withdrawn from graded stimuli according to the procedure of S. R. Chaplan, J. W. Pogrel, T. L. Yaksh, Role of Voltage-Dependent Calcium Channel Subtypes in Experimental Tactile Allodynia, *J. Pharmacol. Exp. Ther.* 1994, 269, 1117–1123. Normal rats can withstand at least 15 g of pressure without responding. Operated rats, however, can respond to as little as 0.25 g of pressure. The surgery was deemed successful if the animal responded with a PWT of less than 4 g of pressure applied to the affected paw.

The sham operation consisted of a similar surgery; the spinal nerve was visualized without being ligated. These animals were also tested for mechanical allodynia and showed no response to greater than 15 g of force applied to the ipsilateral paw. The results of the assay were expressed as percent of the maximum possible effect (% MPE), calculated as the PWT at the time of testing minus the baseline PWT divided by the maximum PWT (15 g) minus the baseline PWT times 100.

The compounds of the present invention indicated in Table 1 were tested for activity against neuropathic pain by being dissolved or suspended in either water or hydroxypropyl methylcellulose, respectively. Postoperative animals between 14 to 42 days were fasted overnight prior to dosing. Animals were orally dosed and dosage volumes were calculated on a 4 mL/kg basis. The screening dose employed was 30 mg/kg.

The compounds of the present invention listed in Table 1 include compounds of the formula:

TABLE 1

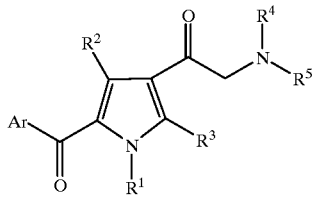

wherein Ar, $R^1$, $R^2$, $R^3$, $R^4$ and $R^5$ are selected concurrently from the group consisting of:

| Cpd # | Ar | $R^1$ | $R^2$ | $R^3$ | $R^4$, $R^5$ | % MPE |
|---|---|---|---|---|---|---|
| 9-3 | 4-ClPh | $CH_3$ | $CH_3$ | $CH_3$ | —$(CH_2)_5$— | 58 |
| 9-4 | 4-ClPh | $CH_3$ | H | H | $C_2H_5$, $C_2H_5$ | 61 |
| 9-32 | 4-ClPh | $CH_3$ | $CH_3$ | $CH_3$ | $C_2H_5$, $C_2H_5$ | 20 |
| 9-39 | 2,4-diClPh | $CH_3$ | $CH_3$ | $CH_3$ | —$(CH_2)_4$— | 19 |
| 9-40 | 4-ClPh | $CH_3$ | $CH_3$ | $CH_3$ | H, $C_2H_5$ | 30* |
| 9-41 | 2-ClPh | $CH_3$ | H | H | 4-[bis(4-fluorophenyl)methylene]-piperidin-1-yl | 65 |
| 9-42 | 4-OMePh | $CH_3$ | H | H | 1,2,3,4-tetrahydro-6,7-dimethoxy-isoquinolin-2-yl | 53 |

*Administered at a dose of 300 mg/kg

The results of the "Chung Model" study are statistically significant and suggest that the compounds of the present invention are effective in reducing neuropathic pain. For treating neuropathic pain, the compounds of the present invention may be employed at a daily dosage in the range of about 30 to 2000 mg, usually in 2 to 4 divided doses, for an average adult human. A unit dose would contain about 10 to 500 mg of the active ingredient. More generally, for mammals, the treatment would comprise the daily administration of from about 0.5 mg/kg to about 50 mg/kg.

To prepare the pharmaceutical compositions of this invention, one or more compounds of the present invention are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful, suppository and the like, from about 10 to about 500 mg of the active ingredient.

The following examples are offered by way of illustration and not by way of limitation.

EXAMPLE 1

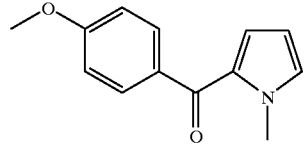

(4-Methoxyphenyl)(1-methyl-1H-pyrrol-2-yl)-methanone

A solution of 5 g (0.06 mole) N-methylpyrrole and 13.3 g (0.078 mole) of 4-methoxybenzoyl chloride in 50 mL of dry toluene was heated under reflux overnight with an argon stream bubbling through the reaction mixture. After cooling, 40 mL of 20% 3-dimethylaminopropylamine in $H_2O$ was added and the mixture stirred for 45 minutes. Diethyl ether was added and the organic solution was washed with 1N HCl, $NaHCO_3$, water, brine and dried ($MgSO_4$). The solvent was evaporated in vacuo and the residue recrystallized from ethanol to give 3.68 g of product: mp. 66–68° C.; mass spectrum ($CH_4$-Cl) m/z=216 (M+1); NMR ($CDCl_3$) d 7.85 (d, 2H); 6.9–7.1 (d,s, 3H); 6.7 (d, 1H); 6.15 (d, 1H); 4.1 (s, 3H); 3.9 (s, 3H). Anal Calcd for $C_{13}H_{13}NO_2$: C, 72.54; H, 6.09; N, 6.51. Found: C, 72.59; H, 6.06; N. 6.43.

EXAMPLE 2

By the procedure of Example 1, employing the appropriate aroyl chloride in place of 4-methoxybenzoylchloride, the following products were produced:

(2-chlorophenyl)(1-methyl-1H-pyrrol-2-yl)methanone: mp 55–57° C.

(1-methyl-1H-pyrrol-2-yl)(4-nitrophenyl)-methanone: mp 148–150° C.

(3-chlorophenyl)(1-methyl-1H-pyrrol-2-yl)-methanone: bp 115–116° C. (0.004 Torr).

EXAMPLE 3

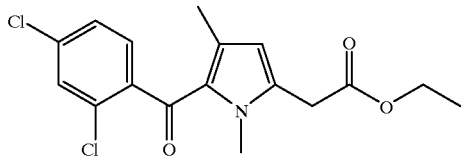

Ethyl 5-(2,4-dichlorobenzoyl)-1,4-dimethyl-1H-pyrrole-2-acetate

A solution of 50 g (0.276 mole) of ethyl 1,4-dimethyl-1H-pyrrole-2-acetate and 64 g (0.303 mole) of 2,4-dichlorobenzoyl chloride in 310 mL of xylene was heated under reflux for 4 h under argon. After cooling, a 20% solution of 3-dimethylaminopropylamine in $H_2O$ was added and stirred one hour. The organic layer was washed twice with 1N HCl, water, brine, and dried ($MgSO_4$). Evaporation of the solvent in vacuo gave a solid which was recrystallized from methanol to give 79.39 g of product: mp 90–92° C.; mass spectrum (Cl—CH$_4$) m/z=354 (M+1); NMR 300 MHz (CDCl$_3$) d 7.5 (s, 1H); 7.3 (dd, 2H); 6.0 (s, 1H); 4.2 (q, 2H); 3.9 (s, 3H); 3.65 (s, 2H); 1.6 (s, 3H); 1.25 (t, 3H). Anal Calcd for C$_{17}$H$_{17}$Cl$_2$NO$_3$: C, 57.64; H, 4.84; N, 3.95. Found: C, 57.52; H, 4.60; N, 3.80.

EXAMPLE 4

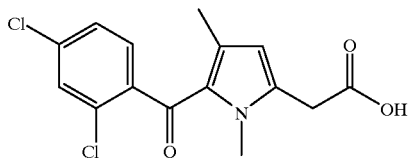

5-(2,4-Dichlorobenzoyl)-1,4-dimethyl-1H-pyrrole-2-acetic Acid

A solution of 2.38 mL (1.1 eq) of 1N NaOH was added dropwise to a refluxing solution of 76.89 g (0.217 mole) of ethyl 5-(2,4-dichlorobenzoyl)-1,4-dimethyl-1H-pyrrole-2-acetate (3) in 750 mL absolute ethanol. The mixture was heated under reflux for 20 minutes. The reaction was poured into 3N HCl/ice and extracted three times with diethyl ether. The organics were washed with water (twice), brine, and dried (MgSO$_4$). Evaporation of the solvent in vacuo gave a tan oil which was crystallized from acetonitrile to give 63.05 g of product: mp 140–143° C.; mass spectrum (Cl—CH$_4$) m/z=326 (M+1); NMR 300 MHz (Me$_2$SO-d$_6$) d 7.8 (s, 1H); 7.6 (m, 1H); 7.4 (m, 1H); 6.0 (s, 1H); 3.8 (s, 3H); 3.75 (s, 2H); 1.45 (s, 3H). Anal Calcd for C$_{15}$H$_{13}$Cl$_2$NO$_3$: C, 55.24; H, 4.02; N, 4.29. Found: C, 55.47; H, 3.84; N, 4.29.

EXAMPLE 5

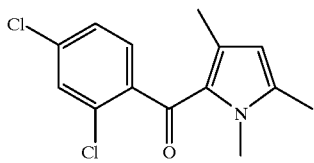

(2,4-Dichlorophenyl)(1,3,5-trimethyl-1H-pyrrol-2-yl)-methanone

A solution of 62.69 g (0.18 mole) 5-(2,4-dichlorobenzoyl)-1,4-dimethyl-1H-pyrrole-2-acetic acid (4) in 550 mL of propionic acid was heated under reflux overnight then poured into water. The solution was extracted three times with diethyl ether. The ether solution was washed successively with NaHCO$_3$, water and brine, and dried (MgSO$_4$). Evaporation of the solvent in vacuo gave a tan solid which was recrystallized from methylcyclohexane: mp 96–98° C.; mass spectrum (Cl—CH$_4$) m/z=282 (M+1); NMR 300 MHz (CDCl$_3$) d 7.5 (s, 1H); 7.35–7.2 (m, 2H); 5.8 (s, 1H); 3.9 (s, 3H); 2.25 (s, 3H); 1.6 (s, 3H). Anal Calcd for C$_{14}$H$_{13}$Cl$_2$NO: C, 59.59; H, 4.64; N, 4.96. Found: C, 59.79; H, 4.39; N, 4.92.

EXAMPLE 6

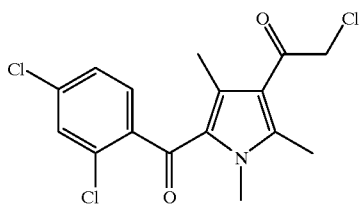

2-Chloro-1-[5-(2,4-Dichlorobenzoyl)-1,2,4-trimethyl-1H-pyrrol-3-yl]-ethanone

A solution of 48.65 g (0.17 mole) of (2,4-dichlorophenyl)(1,3,5-trimethyl-1H-pyrrol-2-yl)-methanone (5) in 480 mL 1,2-dichloroethane was cooled in an ice bath and 53.5 g (0.425 mole) of AlCl$_3$ was added in four portions. A 33.5 mL portion of (0.425 mole) chloroacetyl chloride was added dropwise. The ice bath was removed and the reaction allowed to stir for 3 h under argon. A 10 g sample of AlCl$_3$ was added and the reaction was stirred overnight. The mixture was poured into 1N HCl/ice and the organic layer was separated. The aqueous layer was extracted twice with methylene chloride. The organics were combined and washed with water, NaHCO$_3$, water, brine, and dried (MgSO$_4$). The solvent was evaporated in vacuo and the residue recrystallized from methylcyclohexane to give 53.50 g of product: mp 100–102° C.; mass spectrum (Cl—CH$_4$) m/z=358 (M+1); NMR 300 MHz (CDCl$_3$) d 7.55 (s, 1H); 7.4 (s, 2H); 4.4 (s, 2H); 3.7 (s, 3H); 2.5 (s, 3H); 1.9 (s, 3H). Anal Calcd for C$_{16}$H$_{14}$NO$_2$: C, 53.58; H, 3.93; N, 3.91. Found: C, 53.48; H, 3.81; N, 3.93.

EXAMPLE 7

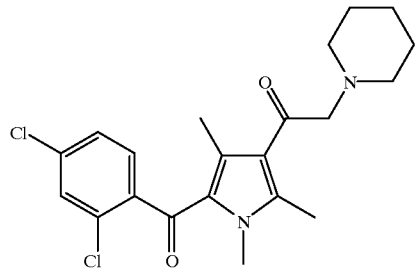

1-[5-(2,4-Dichlorobenzoyl)-1,2,4-trimethyl-1H-pyrrol-3-yl]-2-(1-piperidinyl)-ethanone A solution of 8.0 g (0.022 mole) of 2-chloro-1-[5-(2,4-dichlorobenzoyl)-1,2,4-trimethyl-1H-pyrrol-3-yl]-ethanone (6) and 4.64 mL (0.066 mole) of piperidine in 130 mL of 2-propanol was heated under reflux for 1.5 h. The reaction was cooled and the solvent evaporated in vacuo. The residue was partitioned between diethyl ether and water and the organic solution was extracted twice with 1N HCl. A solid was removed by filtration and the filtrate was made basic with sodium bicarbonate. The mixture was extracted with diethyl ether and the ether solution was washed with water, brine and dried (MgSO$_4$). The solvent was evaporated in vacuo. The product was converted to the hydrochloride salt and recrystallized from 2-propanol to give 5.97 g of product: mp 177–179° C.; mass spectrum (Cl—CH$_4$) m/z=393 (m+1); NMR 300 MHz (Me$_2$SO-d$_6$) d 7.85 (s,1H); 7.6–7.5 (m, 2H); 4.7 (s, 2H); 3.8 (s, 3H); 3.6–3.4 (m, 2H); 3.2–3.0 (m, 2H); 2.6 (s, 3H); 2.0 (br s, 4H); 1.8 (s 3H). Anal Calcd for C$_{20}$H$_{22}$Cl$_2$N$_2$O$_2$: C, 55.22; H, 5.87; N, 6.05. Found: C, 55.06; H, 5.89; N, 6.05.

EXAMPLE 8

Using the procedure of Example 6 and employing the appropriate aryl pyrrolyl methanone in place of (2,4-dichlorphenyl)(1,3,5-trimethyl-1H-pyrrol-2-yl)-methanone and the appropriate y-chloroacyl choride in place of chloroacetyl chloride, there were obtained the following products (8-1 through 8-9) having the formula:

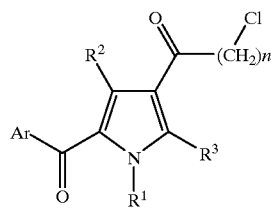

wherein Ar, $R^1$, $R^2$, $R^3$ and n are selected concurrently from the group consisting of:

| No. | Ar | $R^1$ | $R^2$ | $R^3$ | n |
|---|---|---|---|---|---|
| 8-1 | p-ClPh | $CH_3$ | H | H | 1 |
| 8-2 | p-ClPh | $CH_3$ | $CH_3$ | $CH_3$ | 1 |
| 8-3 | o-ClPh | $CH_3$ | H | H | 1 |
| 8-4 | p-$CH_3$OPh | $CH_3$ | H | H | 1 |
| 8-5 | p-$NO_2$Ph | $CH_3$ | H | H | 1 |
| 8-6 | m-ClPh | $CH_3$ | H | H | 1 |
| 8-7 | p-ClPh | H | H | H | 1 |
| 8-8 | p-ClPh | $CH_3$ | H | H | 3 |
| 8-9 | p-Cl | $CH_3$ | $CH_3$ | $CH_3$ | 4 |

They are described as follows:

| No. | M.P. (° C.) | Yield (%) | Formula | Calc'd/ Found |
|---|---|---|---|---|
| 8-1 | 163 | 68.1 | $C_{14}H_{11}Cl_2NO_2$ | C, 56.78; H, 3.74; N, 4.73 |
| | | | | C, 56.63; H, 3.82; N, 4.63 |
| 8-2 | 141–143 | 31 | $C_{16}H_{15}Cl_2NO_2$ | C, 59.28; H, 4.66; N, 4.32 |
| | | | | C, 59.32; H, 4.73; N, 4.33 |
| 8-3 | 121–124 | 91 | $C_{14}H_{11}Cl_2NO_2$ | C, 56.78; H, 3.74; N, 4.73 |
| | | | | C, 56.72; H, 3.66; N, 4.70 |
| 8-4 | 157–159 | 90 | $C_{15}H_{14}ClNO_2$ | C, 61.76; H, 4.84; N, 4.80 |
| | | | | C, 61.51; H, 4.70; N, 4.69 |
| 8-5 | 173–176 | 60 | $C_{14}H_{11}ClN_2O_4$ | C, 54.83; H, 3.61; N, 9.1 |
| | | | | C, 55.11; H, 3.70; N, 9.10 |
| 8-6 | 116–119 | 67 | $C_{14}H_{11}Cl_2NO_2$ | C, 56.78; H, 3.74; N, 4.73 |
| | | | | C, 56.87; H, 3.83; N, 4.77 |
| 8-7 | 196–197 | 91 | $C_{13}H_9Cl_2NO_2$ | C, 55.35; H, 3.22; N, 4.96 |
| | | | | C, 55.76; H, 2.84; N, 4.86 |
| 8-8 | 95–97 | 39 | $C_{16}H_{15}Cl_2NO_2$ | C, 59.28; H, 4.66; N, 4.32 |
| | | | | C, 59.44; H, 4.24; N, 4.24 |
| 8-9 | 60–65 | 79 | $C_{19}H_{21}Cl_2NO_2$ | C, 62.30; H, 5.78; N, 3.82 |
| | | | | C, 62.35; H, 5.74; N, 3.75 |

EXAMPLE 9

Using the procedure of Example 7 and employing the appropriate 1-(5-aroylpyrrol-3-yl)-y-chloroalkanone in place of 2-chloro-1-[5-(2,4-dichlorobenzoyl)-1,2,4-trimethyl-1H-pyrrol-3-yl]-ethanone and the appropriate amine in place of piperidine, there were obtained the following products (9-1 through 9-42) having the formula:

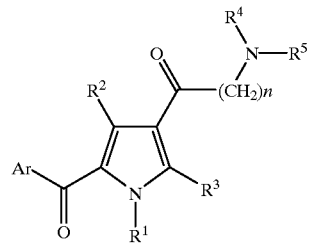

wherein n, $R^1$, $R^2$, $R^3$, $R^4$, $R^5$ and Ar are selected concurrently from the group consisting of:

| No | n | $R^1$ | $R^2/R^3$ | $R^4/R^5$ | Ar |
|---|---|---|---|---|---|
| 9-1 | 1 | $CH_3$ | H/H | cyclohexyl | p-ClPh |
| 9-2 | 1 | $CH_3$ | $CH_3/CH_3$ | morpholinyl | p-ClPh |
| 9-3 | 1 | $CH_3$ | $CH_3/CH_3$ | cyclohexyl | p-ClPh |
| 9-4 | 1 | $CH_3$ | H/H | $CH_2CH_3/CH_2CH_3$ | p-ClPh |
| 9-5 | 1 | $CH_3$ | $CH_3/CH_3$ | cyclopentyl | p-ClPh |

-continued
| No | n | R¹ | R²/R³ | R⁴/R⁵ | Ar |
|---|---|---|---|---|---|
| 9-6 | 1 | CH₃ | CH₃/CH₃ |  | p-ClPh |
| 9-7 | 1 | CH₃ | CH₃/CH₃ | 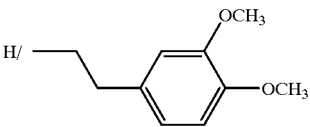 | p-ClPh |
| 9-8 | 1 | CH₃ | H/H |  | p-ClPh |
| 9-9 | 1 | CH₃ | CH₃/CH₃ | 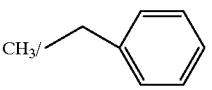 | p-ClPh |
| 9-10 | 1 | CH₃ | H/H |  | o-ClPh |
| 9-11 | 1 | CH₃ | H/H | 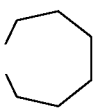 | p-ClPh |
| 9-12 | 1 | CH₃ | H/H |  | o-ClPh |
| 9-13 | 1 | CH₃ | H/H | 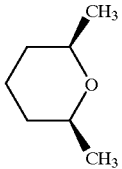 | p-ClPh |
| 9-14 | 1 | CH₃ | H/H | 1-Adamantyl | o-ClPh |
| 9-15 | 1 | CH₃ | H/H | 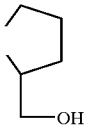 | p-ClPh |
| 9-16 | 1 | CH₃ | H/H | 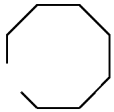 | p-ClPh |
| 9-17 | 1 | CH₃ | H/H |  | p-OCH₃Ph |
| 9-18 | 1 | CH₃ | H/H |  | p-OCH₃Ph |

-continued
| No | n | R¹ | R²/R³ | R⁴/R⁵ | Ar |
|---|---|---|---|---|---|
| 9-19 | 1 | CH₃ | H/H |  | o-ClPh |
| 9-20 | 1 | CH₃ | H/H |  | p-NO₂Ph |
| 9-21 | 1 | CH₃ | H/H |  | p-NO₂Ph |
| 9-22 | 1 | CH₃ | H/H | 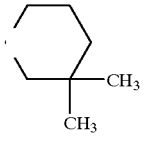 | p-ClPh |
| 9-23 | 1 | CH₃ | H/H |  | m-ClPh |
| 9-24 | 1 | CH₃ | H/H |  | m-ClPh |
| 9-25 | 1 | CH₃ | H/H |  | m-ClPh |
| 9-26 | 1 | H | H/H |  | p-ClPh |
| 9-27 | 1 | H | H/H |  | p-ClPh |
| 9-28 | 1 | CH₃ | H/H | H/CH₂CH₃ | p-ClPh |
| 9-29 | 1 | CH₃ | H/H | CH₂CH₃/CH₂CH₃ | p-OCH₃Ph |
| 9-30 | 1 | CH₃ | H/H |  | p-ClPh |
| 9-31 | 1 | CH₃ | H/H |  | p-ClPh |
| 9-32 | 1 | CH₃ | CH₃/CH₃ | CH₂CH₃/CH₂CH₃ | p-ClPh |
| 9-33 | 1 | CH₃ | H/H |  | p-OCH₃ |
| 9-34 | 1 | CH₃ | CH₃/CH₃ | CH₂CH₃/CH₂CH₃ | 2,4-diClPh |
| 9-35 | 1 | CH₃ | CH₃/CH₃ | CH₃/CH₃ | 2,4-diClPh |

-continued

| No | n | R¹ | R²/R³ | R⁴/R⁵ | Ar |
|---|---|---|---|---|---|
| 9-36 | 1 | $CH_3$ | H/H |  | p-ClPh |
| 9-37 | 4 | $CH_3$ | $CH_3/CH_3$ | $CH_2CH_3/CH_2CH_3$ | p-ClPh |
| 9-38 | 4 | $CH_3$ | $CH_3/CH_3$ |  | p-ClPh |
| 9-39 | 1 | $CH_3$ | $CH_3/CH_3$ |  | 2,4-diClPh |
| 9-40 | 1 | $CH_3$ | $CH_3/CH_3$ | $H/CH_2CH_3$ | p-ClPh |
| 9-41 | 1 | $CH_3$ | H/H | 4-[bis(4-fluorophenyl)-methylene]-piperidin-1-yl | o-ClPh |
| 9-42 | 1 | $CH_3$ | H/H | 1,2,3,4-tetrahydro-6,7-dimethoxy-isoquinolin-2-yl | p-$OCH_3$Ph |

They are described as follows:

| No. | M.P. (° C.) | Formula | Calc'd/Found (C, H, N) | Rxn Solv |
|---|---|---|---|---|
| 9-1 | 114–116 | $C_{19}H_{21}ClN_2O_2$ | 66.18, 6.14, 8.12<br>66.45, 6.12, 7.9 | neat |
| 9-2 | 96–98 | $C_{20}H_{23}ClN_2O_3$ | 64.08, 6.18, 7.47<br>64.14, 6.16, 7.38 | i-PrOH |
| 9-3 | 102–104 | $C_{21}H_{25}ClN_2O_2$ | 61.62, 6.40, 6.84<br>61.58, 6.67, 6.64 | EtOH |
| 9-4 | 182–185 | $C_{18}H_{21}ClN_2O_2$·HCl | 58.54, 6.01, 7.51<br>58.57, 6.00, 7.66 | EtOH |
| 9-5 | 115–117 | $C_{20}H_{23}ClN_2O_2$ | 66.94, 6.46, 7.81<br>67.10, 6.40, 7.76 | i-PrOH |
| 9-6 | 195–197 | $C_{19}H_{18}ClN_3O_2$ | 64.14, 5.10, 11.81<br>64.02, 4.99, 11.75 | i-PrOH |
| 9-7 | 210–213 | $C_{26}H_{29}ClN_2O_4$·HCl | 61.78, 5.98, 5.54<br>61.70, 5.92, 5.48 | i-PrOH |
| 9-8 | 131–135 | $C_{18}H_{19}ClN_2O_3$ | 62.41, 5.53, 8.09<br>62.44, 5.91, 8.05 | i-PrOH |
| 9-9 | 155–156 | $C_{24}H_{25}ClN_2O_2C_2H_2O_2$** | 62.59, 5.45, 5.54<br>62.56, 5.62, 5.61 | i-PrOH |
| 9-10 | 169–171 | $C_{19}H_{21}ClN_2O_2C_4H_4O_4$* | 59.94, 5.47, 6.08<br>59.68, 5.40, 5.98 | i-PrOH |
| 9-11 | 195–198 | $C_{20}H_{23}ClN_2O_2HCl\ 0.25H_2O$ | 60.08, 6.18, 7.01, $H_2O$ 1.13<br>60.02, 6.16, 7.01, $H_2O$ 1.29 | i-PrOH |
| 9-12 | 113–116 | $C_{18}H_{19}ClN_2O_2$·HCl | 58.87, 5.49, 7.63<br>59.02, 5.53, 7.58 | i-PrOH |
| 9-13 | 258–260 | $C_{20}H_{23}ClN_2O_3$·HCl | 58.40, 5.88, 6.81<br>58.17, 5.85, 6.76 | i-PrOH |
| 9-14 | 248 (d) | $C_{24}H_{27}N_2O_2$·HCl·0.25$H_2O$ | 63.79, 6.36, 6.20<br>63.79, 6.31, 6.10, $H_2O$ 0.25 | i-PrOH |
| 9-15 | 87–88 | $C_{19}H_{21}ClN_2O_3 0.8C_4H_4O_4$-2/3$H_2O$* | 57.93, 5.28, 5.87<br>57.46, 5.54, 5.83, KF 4.43 | i-PrOH |
| 9-16 | 211–213 | $C_{21}H_{25}ClN_2O_2$·HCl 0.25$H_2O$ | 60.95, 6.45, 6.77<br>61.13, 6.51, 6.90 | i-PrOH |
| 9-17 | 136–138 | $C_{18}H_{17}N_3O_3$ | 66.86, 5.30, 13.00<br>66.90, 5.31, 12.87 | i-PrOH |
| 9-18 | 190–192 | $C_{20}H_{24}N_2O_3$·HCl | 63.74, 6.69, 7.43<br>63.55, 6.66, 7.34 | i-PrOH |
| 9-19 | 125–127 | $C_{18}H_{19}ClN_2O_3$ | 62.34, 5.52, 8.08<br>62.57, 5.49, 8.04 | i-PrOH |

-continued

| No. | M.P. (° C.) | Formula | Calc'd/Found (C, H, N) | Rxn Solv |
|---|---|---|---|---|
| 9-20 | 141–143 | $C_{18}H_{19}N_3O_5$ | 60.50; 5.36, 11.76<br>60.59; 5.24, 11.67 | i-PrOH |
| 9-21 | 225–227 | $C_{19}H_{21}N_3O_4$-HCl | 58.24, 5.66, 10.72<br>58.20, 5.79, 10.52 | i-PrOH |
| 9-22 | 105–107 | $C_{21}H_{25}ClN_2O_2$ | 67.64, 6.76, 7.51<br>67.67, 6.74, 7.58 | i-PrOH |
| 9-23 | 190–193 | $C_{19}H_{21}ClN_2O_2$-HCl | 59.85, 5.82, 7.35<br>59.92, 5.85, 7.41 | i-PrOH |
| 9-24 | 243–245 | $C_{18}H_{19}ClN_2O_2$—$HClO_4$ | 50.13, 4.67, 6.50<br>50.21, 4.65, 6.50 | neat |
| 9-25 | 198–200 | $C_{18}H_{19}ClN_2O_3$-HCl | 56.41, 5.27, 7.31<br>56.49, 5.24, 7.30 | i-PrOH |
| 9-26 | 242–245 | $C_{17}H_{17}ClN_2O_2$-$HClO_4$ | 48.94, 4.35, 6.71<br>49.01, 4.38, 6.72 | i-PrOH |
| 9-27 | 173–176 | $C_{17}H_{17}ClN_2O_3$ | 61.35, 5.10, 8.42<br>61.21, 5.13, 8.59 | i-PrOH |
| 9-28 | 259–262 | $C_{16}H_{17}ClN_2O_2$-HCl 0.25$H_2O$ | 55.58, 5.39, 8.10<br>55.93, 5.56, 8.07 | i-PrOH |
| 9-29 | 165–168 | $C_{19}H_{24}N_2O_3$-HCl | 62.55, 6.91, 7.68<br>62.25, 6.93, 7.60 | i-PrOH |
| 9-30 | 118–122 | $C_{18}H_{19}ClN_2O_2$ | 65.35, 5.79, 847<br>65.29, 5.85 | neat |
| 9-31 | 173–175 | $C_{17}H_{17}ClN_2O_2$—$C_2H_2O_4$ | 56.10, 4.71, 6.89<br>55.71, 4.68, 6.82 | i-PrOH |
| 9-32 | 176–178 | $C_{20}H_{25}ClN_2O_2$ 1.5$C_4H_4O_4$-0.1EtOH* | 58.31, 5.91, 5.18<br>57.96, 5.85, 5.18 | i-PrOH |
| 9-33 | 114–115 | $C_{19}H_{22}N_2O_3$-HCl-0.6$H_2O$ | 61.07, 6.53, 7.50<br>60.74, 6.83, 7.29 | i-PrOH |
| 9-34 | 165–168 | $C_{20}H_{24}Cl_2N_2O_2C_4H_4O_4$* | 56.37, 5.52, 5.48<br>56.34, 5.70, 5.43 | i-PrOH |
| 9-35 | 119 | $C_{18}H_{20}Cl_2N_2O$-HCl 0.75$H_2O$ | 51.75, 5.48, 6.55,<br>$H_2O$ 3.71<br>51.77, 5.44, 6.71,<br>$H_2O$ 3.31 | toluene |
| 9-36 | 218–219 | $C_{18}H_{16}ClN_3O_2$ | 63.25, 4.72, 12.29<br>63.20, 4.82, 12.27 | i-PrOH |
| 9-37 | 71–73 | $C_{23}H_{31}ClN_2O_2$ | 68.56, 7.75, 6.95<br>68.52, 7.86, 6.90 | neat |
| 9-38 | 177–178 | $C_{24}H_{31}ClN_2O_2$—$C_4H_4O_4$* | 63.33, 6.64, 5.28<br>63.25, 6.67, 5.23 | i-PrOH |
| 9-39 | 177–179 | $C_{20}H_{22}Cl_2N_2O$—HCl 0.4$H_2O$ | 55.22, 5.87, 6.05,<br>$H_2O$ 1.55<br>55.06, 5.39, 6.05,<br>$H_2O$ 1.56 | i-PrOH |
| 9-40 | 259–262 | $C_{16}H_{17}ClN_2O_2$—HCl 0.25$H_2O$ | 55.58, 5.39, 8.10,<br>$H_2O$ 1.30<br>55.93, 5.56, 8.07,<br>$H_2O$ 1.39 | MeOH/<br>EtOH |
| 9-41 | 189–191 | $C_{32}H_{27}ClF_2N_2O_2$—HCl 0.16$H_2O$ | 65.77, 4.88, 4.79<br>65.85, 4.89, 4.80 | i-PrOH/<br>DIPEA* |
| 9-42 | 248–251 | $C_{26}H_{28}N_2O_5$—HCl 0.4$H_2O$-0.25EtOH | 63.15, 6.27, 5.56<br>63.27, 6.52, 5.51 | i-PrOH/<br>DIPEA |

*DIPEA: diisopropylethylamine

EXAMPLE 10

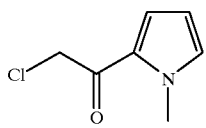

2-Chloro-1-(1-Methyl-1H-pyrrol-2-yl)-ethanone

A solution of 15 g (0.186 mole) N-methylpyrrole and 19.2 mL (0.186 mole) chloroacetyl chloride in 600 mL dry THF was heated under reflux overnight with a nitrogen stream bubbling through the reaction mixture. After cooling, the organics were washed with water, 1N NaOH, water, brine and dried ($MgSO_4$). Evaporation of the solvent gave 31.2 g of a green solid: mp (decomp.) 280° C.; NMR 300 MHz ($CDCl_3$) d 7.05 (d, 1H); 6.95 (s, 1H); 6.2 (m, 1H); 4.5 (s, 2H); 3.9 (s, 3H).

EXAMPLE 11

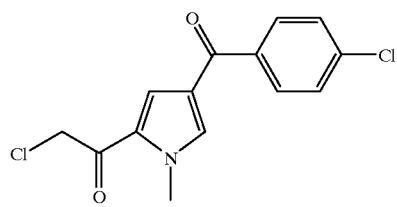

2-Chloro-1-[4-(4-chlorobenzoyl)-1-methyl-1H-pyrrol-2-yl]-ethanone solution of 30 g (0.19 mole) of 2-chloro-1-(1-methyl-1H-pyrrol-2-yl)-ethanone (10) in 180 mL 1,2-dichloroethane (DCE) under an argon atmosphere was cooled in an ice bath and 60 g $AlCl_3$ (0.45 mole) was added in portions. After stirring for 10 minutes, a solution of 24 mL (0.19 mole)

4-chlorobenzoyl chloride in 110 mL DCE was added dropwise. The ice bath was removed and the reaction was stirred at room temperature overnight. The reaction was poured into 1N HCl/ice and the aqueous layer was extracted three times with methylene chloride. The organics solutions were combined, washed with water, 1N NaOH, water, brine, and dried (MgSO$_4$). Evaporation of the solvent in vacuo gave a solid which was recrystallized from ethyl acetate/methylcyclohexane to give 27.67 g of a solid: mp 130–132° C.; NMR 300 MHz (CDCl$_3$) d 7.8 (m, 2H); 7.6–7.4 (m, 4H); 4.5 (s, 2H); 4.0 (s, 3H). Anal Calcd for $C_{14}H_{11}Cl_2NO_2$: C, 56.78; H, 3.74; N, 4.73. Found: C, 56.72; H, 3.76; N, 4.73.

EXAMPLE 12

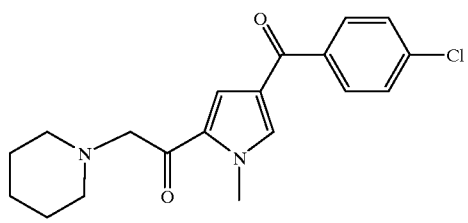

1-[4-(4-Chlorobenzoyl)-1-methyl-1H-pyrrol-2-yl]-2-(1-piperidinyl)-ethanone

A solution of 4 g (0.013 mole) of 2-chloro-1-[4-(4-chlorobenzoyl)-1-methyl-1H-pyrrol-2-yl]-ethanone (11) and 4.08 mL (0.039 mole) of piperidine in 60 mL 2-PrOH was heated under reflux for 1 h. The solvent was evaporated in vacuo and the residue was taken up in diethyl ether/THF, washed with water, brine, and dried (MgSO$_4$). Evaporation of the solvent gave a tan solid which was recrystallized from 2-PrOH to give 3.65 g of product: mp 129–130° C.; mass spectrum (Cl—CH$_4$) m/z=345 (M+1); NMR 300 MHz (CDCl$_3$) d 7.8 (m, 2H); 7.6 (s, 1H); 7.45 (d, 2H); 7.35 (s, 1H); 4.0 (s, 3H); 3.6 (s, 2H); 2.5 (br s, 4H); 1.6 (m, 4H); 1.4 (m, 2H). Anal Calcd for $C_{19}H_{21}Cl_2N_2O_2$: C, 66.18; H, 6.14; N, 8.12. Found: C, 66.25; H, 6.16; N, 8.08.

EXAMPLE 13

By the procedure of example 12 and employing the appropriate amine in place of piperidine the following products were prepared:

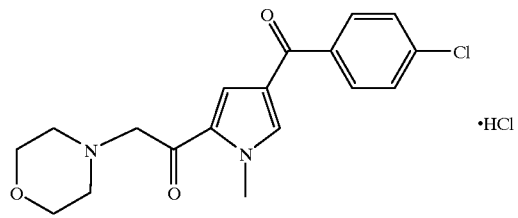

1-[4-(4-Chlorobenzoyl)-1-methyl-1H-2pyrrol-2-yl]-2-(1-morpholino)-ethanone Hydrochloride (13-1)

mp 264–267° C. Anal Calcd for $C_{18}H_{19}ClN_2O_3$-HCl: C, 56.41; H, 5.26; N, 7.31. Found: C, 56.14; H, 5.50; N, 7.17.

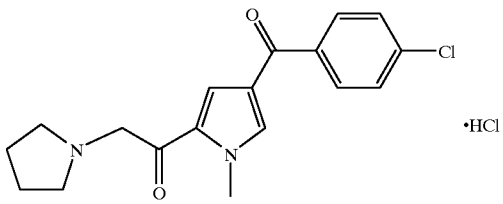

1-[4-(4-Chlorobenzoyl)-1-methyl-1H-pyrrol-2-yl]-2-(1-pyrrolidinyl)-ethanone Hydrochloride (13-2)
mp 265–267° C. Anal Calcd for $C_{18}H_{19}ClN_2O_2$-HCl: C, 58.87; H, 5.49; N, 7.63. Found: C, 58.83; H, 5.66; N, 7.54.

EXAMPLE 14

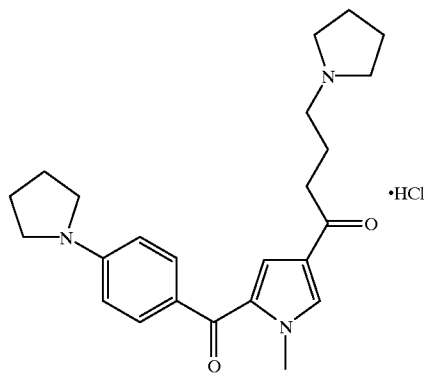

4-(Pyrrolidin-1-yl)-1-[5-(4-pyrrolidin-1-ylbenzoyl)-1-methyl-1H-pyrrol-3-yl]-butanone Hydrochloride
A 10 g (0.03 mole) sample of 4-chloro-1-[5-(4-chlorobenzoyl)-1-methyl-1H-pyrrol-3-yl]-butanone was added to 18 mL (0.216 mole) of pyrrolidine and the mixture heated under reflux for 4 h. The solvent was evaporated in vacuo and the residue triturated with Et$_2$O. The mixture was filtered and the filtrate treated with ethereal HCl to give the salt. Recrystallization from CH$_3$CN gave 1.18 g (9% yield) of a yellow solid: mp 203–206° C. $^1$H NMR (Me$_2$SO-d$_6$) d 1.85–2.05 (m, 10H); 2.87–3.05 (m, 4H); 3.1–3.15 (m, 2H); 3.3–3.4 (m, 4H); 3.45–3.55 (broad s, 2H); 3.9 (s, 3H); 6.62 (d, 2H); 6.96 (s,1H); 7.72 (d, 2H); 7.92 (s, 1H). Anal Calcd for $C_{24}H_{31}N_3O_2$-HCl-0.4CH$_3$CN: C, 66.73; H, 7.50; N, 10.67. Found: C, 66.34; H, 7.43; N, 10,33.

EXAMPLE 15

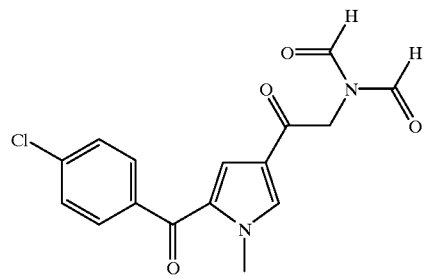

2-[(Bis-formyl)amino]-1-[5-(4-chlorobenzoyl)-1-methyl-1H-pyrrol-3-yl]-ethanone
A solution of 10 g (0.034 mole) of 2-chloro-1-[5-(4-chlorobenzoyl)-1-methyl-1H-pyrrol-3-yl]-ethanone and 3.8 g (0.041 mole) sodium diformylamide in 80 mL acetonitrile was heated under reflux overnight under argon. An additional 2.0 g portion of sodium diformylamide was added and reflux was continued for 1.5 hrs. After evaporation of the solvent in vacuo the residue was passed through a flash column (silica gel, 3:1 hexane:acetone the 2:1 hexane:acetone) to give 6.18 g of a solid. mp 279–282° C. 260° C. decomp. mass spectrum (CI—CH$_4$) m/z=333 (M+1). NMR 300 MHz (CDCl$_3$) d 9.0 (s, 2H); 7.8 (d, 2H); 7.55 (s, 1H); 7.45 (d, 2H); 7.1 (s, 1H); 4.85 (s, 2H); 4.1 (s, 3H).

EXAMPLE 16

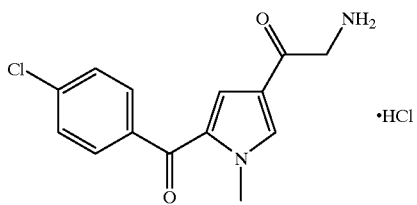

2-Amino-1-[5-(4-Chlorobenzoyl)-1-methyl-1H-pyrrol-3-yl]-ethanone Hydrochloride 6.18 g (0.0186 mole) 2-[(Bis-formyl)amino]-1-[5-(4-chlorobenzoyl)-1-methyl-1H -pyrrol-3-yl]-ethanone was stirred 3 days in 5% HCl/EtOH. A 0.5 mL portion of conc. HCL was added and the reaction stirred for two more days. The solid was collected by filtration. The solid was stirred in refluxing methanol and the undissolved solid collected by filtration and discarded. The filtrate was cooled to room temperature and diethyl ether was added. The solid was collected. It was twice treated with boiling methanol to give pure product: mp 290° C. (decomp.); mass spectrum (CH$_4$-Cl) m/z=277 (M+1); NMR (Me$_2$SO-d$_6$) d 8.2 (br s, 4H); 7.85 (d, 2H); 7.6 (d, 2H); 7.2 (s, 1H); 4.3 (s, 2H); 4.0 (s 3H). Anal Calcd for C$_{14}$H$_{13}$ClN$_2$O$_2$-HCl: C, 53.69; H, 4.51; N, 8.94. Found: C, 53.91; H, 4.4.1; N, 8.76.

What is claimed is:

1. A method for the treatment of neuropathic pain comprising the step of administering to a mammal suffering from such condition an effective amount, in a pharmaceutically acceptable carrier, of an active compound of the formula:

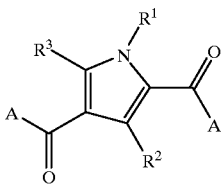

wherein,

A is

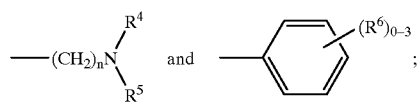

n is an integer from 1 to 5;

R$^1$ is selected from the group consisting of H and C$_{1-4}$alkyl;

R$^2$ and R$^3$ are selected from the group consisting of H and C$_{1-4}$alkyl;

R$^4$ and R$^5$ are independently selected from the group consisting of H, C$_{1-4}$alkyl, phenyl C$_{1-4}$ alkyl and substituted phenyl C$_{1-4}$ alkyl where the substituent is on phenyl and selected from the group consisting of methyl and methoxy, or in the alternative, are fused and together with said nitrogen form a heterocyclic ring selected from the group consisting of 4-[bis(4-fluorophenyl)methylene]-piperidin-1-yl, 1,2,3,4-tetrahydro-6,7-dimethoxy-isoquinolin-2-yl,

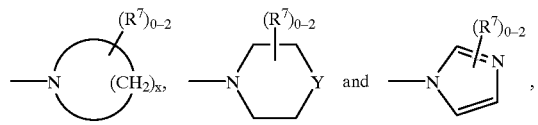

wherein Y is S or O, x is 3 to 7 and R$^7$ is selected from the group consisting of methyl and hydroxymethyl; and R$^6$ is selected from the group consisting of halo, C$_{1-4}$ alkyl, C$_{1-4}$ alkoxy, hydroxy, nitro, amino, C$_{1-4}$ acylamino, cyano, trihaloC$_{1-4}$alkyl, C$_{1-4}$alkylsulfonyl, C$_{1-4}$alkylsulfinyl, and C$_{1-4}$ acyl, including pharmaceutically acceptable acid addition salts thereof.

2. The method of claim 1 wherein R$^1$ of said formula of said active compound is selected from the group consisting of hydrogen, methyl, ethyl, n-propyl and i-propyl.

3. The method of claim 1 wherein R$^2$ and R$^3$ of said formula of said active compound are independently selected from the group consisting of hydrogen, methyl, ethyl, n-propyl and i-propyl.

4. The method of claim 1 wherein R$^4$ and R$^5$ of said formula of said active compound, where independently selected, are selected from the group consisting of hydrogen, methyl, ethyl, n-propyl, i-propyl, benzyl and 2-phenyleth-1-yl where the phenyl ring may be mono- or di-substituted with a substituent selected from the group of methyl and methoxy.

5. The method of claim 1 wherein R$^4$ and R$^5$ of said formula of said active compound, where fused and depicted together with nitrogen, are selected from the group consisting of 4-[bis(4-fluorophenyl)methylene]-piperidin-1-yl, 1,2,3,4-tetrahydro-6,7-dimethoxy-isoquinolin-2-yl,

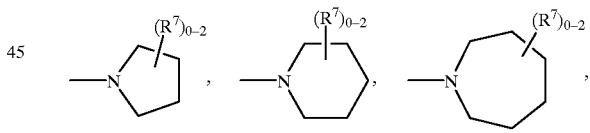

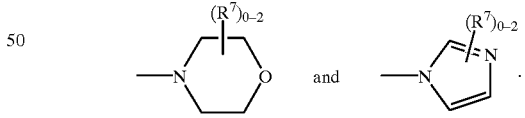

6. The method of claim 1 wherein R$^6$ of said formula of said active compound is selected from the group consisting of bromine, chlorine, methyl, ethyl, methoxy, ethoxy, hydroxy, nitro, amino, formylamino, acetylamino, cyano, perfluoromethyl, 3,3,3-trifluoropropyl, methylsulfonyl, methylsulfinyl, formyl and acetyl.

7. The method of claim 1 wherein said pharmaceutically acceptable salt of said formula of said active compound is selected from the group consisting of hydrochloride, sulfate, phosphate, methane sulfonate, fumarate, maleate, citrate and lactate.

8. The method of claim 1 wherein said formula of said active compound has the formula:

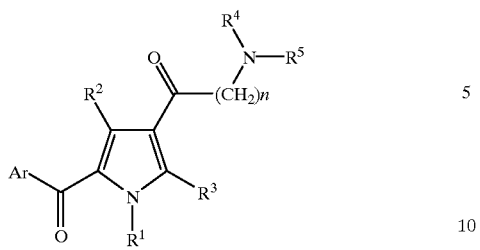

wherein n, $R^1$, $R^2$, $R^3$, $R^4$, $R^5$ and Ar are selected in concert from the group consisting of:

| n | $R^1$ | $R^2/R^3$ | $R^4/R^5$ | Ar |
|---|-------|-----------|-----------|-----|
| 1 | $CH_3$ | H/H | cyclohexyl | p-ClPh; |
| 1 | $CH_3$ | $CH_3/CH_3$ | morpholinyl | p-ClPh; |
| 1 | $CH_3$ | $CH_3/CH_3$ | cyclohexyl | p-ClPh; |
| 1 | $CH_3$ | H/H | $CH_2CH_3/CH_2CH_3$ | p-ClPh; |
| 1 | $CH_3$ | $CH_3/CH_3$ | cyclopentyl | p-ClPh; |
| 1 | $CH_3$ | $CH_3/CH_3$ | pyrrolyl (N-containing) | p-ClPh; |
| 1 | $CH_3$ | $CH_3/CH_3$ | H/ CH$_2$CH$_2$-(3,4-dimethoxyphenyl) | p-ClPh; |
| 1 | $CH_3$ | H/H | morpholinyl | p-ClPh; |
| 1 | $CH_3$ | $CH_3/CH_3$ | $CH_3$/ CH$_2$-phenyl | p-ClPh; |
| 1 | $CH_3$ | H/H | cyclohexyl | o-ClPh; |
| 1 | $CH_3$ | H/H | cycloheptyl | p-ClPh; |

-continued
| n | R¹ | R²/R³ | R⁴/R⁵ | Ar |
|---|----|----|----|----|
| 1 | CH₃ | H/H |  | o-ClPh; |
| 1 | CH₃ | H/H | 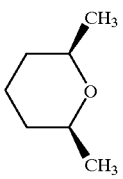 | p-ClPh; |
| 1 | CH₃ | H/H | 1-Adamantyl | o-ClPh; |
| 1 | CH₃ | H/H |  | p-ClPh; |
| 1 | CH₃ | H/H | 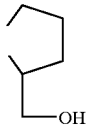 | P-ClPh; |
| 1 | CH₃ | H/H |  | p-OCH₃Ph; |
| 1 | CH₃ | H/H |  | p-OCH₃Ph; |
| 1 | CH₃ | H/H |  | o-ClPh; |
| 1 | CH₃ | H/H |  | p-NO₂Ph; |
| 1 | CH₃ | H/H |  | p-NO₂Ph; |
| 1 | CH₃ | H/H |  | p-ClPh; |
| 1 | CH₃ | H/H |  | m-ClPh; |
| 1 | CH₃ | H/H | 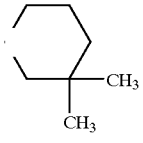 | m-ClPh; |

-continued

| n | R¹ | R²/R³ | R⁴/R⁵ | Ar |
|---|---|---|---|---|
| 1 | CH₃ | H/H |  | m-ClPh; |
| 1 | H | H/H |  | p-ClPh; |
| 1 | H | H/H |  | p-ClPh; |
| 1 | CH₃ | H/H | H/CH₂CH₃ | p-ClPh; |
| 1 | CH₃ | H/H | CH₂CH₃/CH₂CH₃ | p-OCH₃Ph; |
| 1 | CH₃ | H/H |  | p-ClPh; |
| 1 | CH₃ | H/H |  | p-ClPh; |
| 1 | CH₃ | CH₃/CH₃ | CH₂CH₃/CH₂CH₃ | p-ClPh; |
| 1 | CH₃ | H/H |  | p-OCH₃; |
| 1 | CH₃ | CH₃/CH₃ | CH₂CH₃/CH₂CH₃ | 2,4-diClPh; |
| 1 | CH₃ | CH₃/CH₃ | CH₃/CH₃ | 2,4-diClPh; |
| 1 | CH₃ | H/H |  | p-ClPh; |
| 4 | CH₃ | CH₃/CH₃ | CH₂CH₃/CH₂CH₃ | p-ClPh; |
| 4 | CH₃ | CH₃/CH₃ |  | p-ClPh; |
| 1 | CH₃ | CH₃/CH₃ |  | 2,4-diClPh; |
| 1 | CH₃ | CH₃/CH₃ | H/CH₂CH₃ | p-ClPh; |
| 1 | CH₃ | H/H | 4-[bis(4-fluorophenyl)-methylene]-piperidin-1-yl | o-ClPh; |
| 1 | CH₃ | H/H | 1,2,3,4-tetrahydro-6,7-dimethoxy-isoquinolin-2-yl | p-OCH₃Ph; |
| 1 | CH₃ | CH₃/CH₃ |  | 2,4-diClPh; |
| 3 | CH₃ | H/H |  | p-pyrrolidin-1-yl-Ph; | and

-continued
| n | R[1] | R[2]/R[3] | R[4]/R[5] | Ar |
|---|------|-----------|-----------|-----|
| 1 | CH₃ | H/H | H/H | p-ClPh. |
9. The method of claim 1 wherein said active compound is selected from the group consisting of:
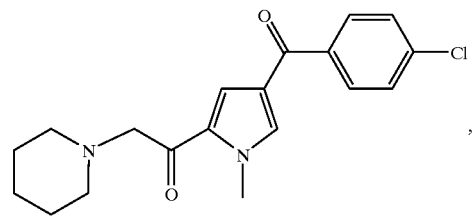
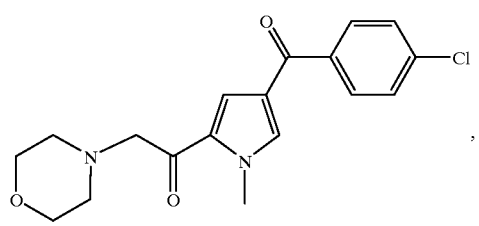
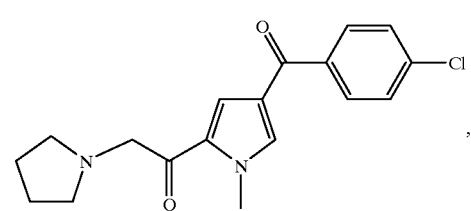
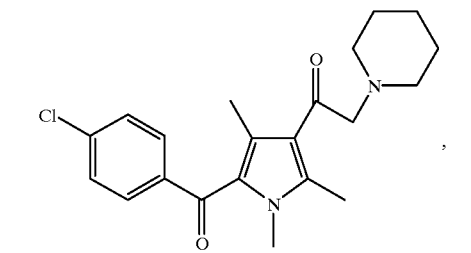
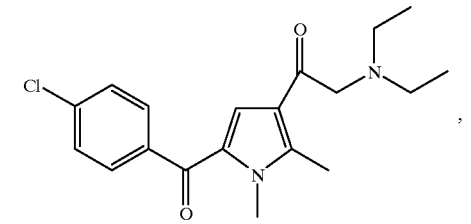
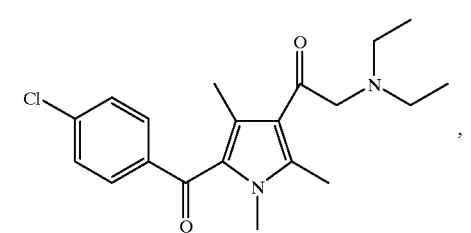
-continued
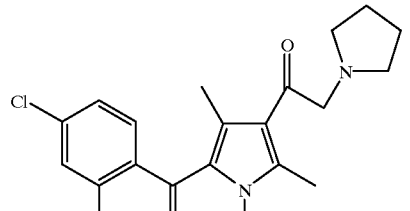
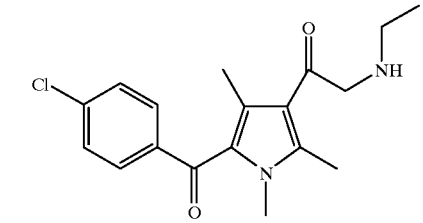
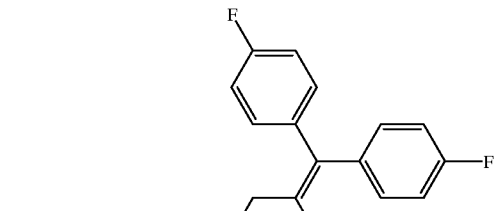
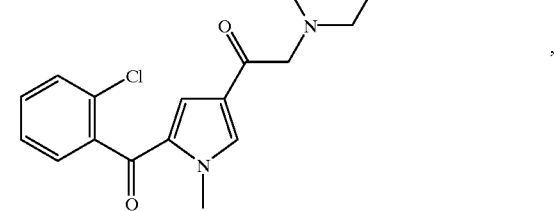
and
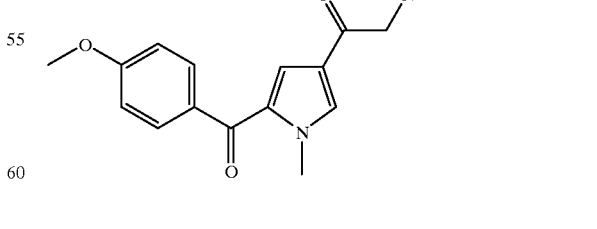
* * * * *